US009896929B2

(12) United States Patent
Farhadiroushan et al.

(10) Patent No.: US 9,896,929 B2
(45) Date of Patent: Feb. 20, 2018

(54) ACOUSTIC ILLUMINATION FOR FLOW-MONITORING

(71) Applicant: Silixa Ltd., Elstree Hertfordshire (GB)

(72) Inventors: Mahmoud Farhadiroushan, Elstree Hertfordshire (GB); Tom Parker, Elstree Hertfordshire (GB); Daniel Finfer, Elstree Hertfordshire (GB); Veronique Mahue, Elstree Hertfordshire (GB)

(73) Assignee: Silixa Ltd., Elstree Hertfordshire (GB)

( * ) Notice: Subject to any disclaimer, the term of this patent is extended or adjusted under 35 U.S.C. 154(b) by 181 days.

(21) Appl. No.: 14/440,138

(22) PCT Filed: Nov. 1, 2013

(86) PCT No.: PCT/GB2013/052875
§ 371 (c)(1),
(2) Date: May 1, 2015

(87) PCT Pub. No.: WO2014/068334
PCT Pub. Date: May 8, 2014

(65) Prior Publication Data
US 2015/0285064 A1 Oct. 8, 2015

(30) Foreign Application Priority Data
Nov. 2, 2012 (GB) .................................. 1219797.6

(51) Int. Cl.
*G01N 29/04* (2006.01)
*E21B 47/12* (2012.01)
(Continued)

(52) U.S. Cl.
CPC ...... *E21B 47/123* (2013.01); *E21B 47/02208* (2013.01); *G01F 1/7086* (2013.01);
(Continued)

(58) Field of Classification Search
CPC ........ E21B 47/123; E21B 47/16; E21B 47/10; G01N 29/024; G01N 29/46; G01N 29/07;
(Continued)

(56) References Cited

U.S. PATENT DOCUMENTS 3,848,460 A * 11/1974 Bantz .................. G01H 5/00
73/597
5,406,530 A 4/1995 Yamamoto
(Continued)

FOREIGN PATENT DOCUMENTS

GB        2486583 A      6/2012
WO   WO-2009056855 A1   5/2009
(Continued)

OTHER PUBLICATIONS

Australian Government, IP Australia, Patent Examination Report No. 1 for AU Application No. 2013340502, dated Nov. 4, 2016.
(Continued)

*Primary Examiner* — Helen Kwok
(74) *Attorney, Agent, or Firm* — Honigman Miller Schwartz and Cohn LLP; Matthew H. Szalach; Jonathan P. O'Brien

(57) ABSTRACT

Externally generated noise can be coupled into a fluid carrying structure such as a pipe, well, or borehole so as to artificially acoustically "illuminate" the pipe, well, or borehole, and allow fluid flow in the structure or structural integrity to be determined. In the disclosed system, externally generated noise is coupled into the structure being monitored at the same time as data logging required to undertake the monitoring is performed. This has three effects. First, the externally generated sound is coupled into the structure so as to "illuminate" acoustically the structure to allow data to be collected from which fluid flow may be determined, and secondly the amount of data that need be
(Continued)

collected is reduced, as there is no need to log data when the structure is not being illuminated. Thirdly, there are signal processing advantages in having the data logging being undertaken only when the acoustic illumination occurs.

2 Claims, 13 Drawing Sheets

(51) Int. Cl.
| | |
|---|---|
| *G01F 1/66* | (2006.01) |
| *G01P 5/24* | (2006.01) |
| *G01N 29/024* | (2006.01) |
| *G01N 29/46* | (2006.01) |
| *E21B 47/022* | (2012.01) |
| *G01F 1/708* | (2006.01) |

(52) U.S. Cl.
CPC ........... *G01N 29/024* (2013.01); *G01N 29/46* (2013.01); *G01P 5/241* (2013.01); *G01N 2291/02836* (2013.01); *G01N 2291/106* (2013.01)

(58) Field of Classification Search
CPC ... G01N 29/449; G01F 1/7086; G01F 1/7082; G01F 1/74
See application file for complete search history.

(56) References Cited

U.S. PATENT DOCUMENTS

| | | | |
|---|---|---|---|
| 6,456,566 B1 | 9/2002 | Aronstam | |
| 7,197,942 B2* | 4/2007 | Gysling | G01F 1/7082 |
| | | | 73/24.01 |
| 7,249,525 B1* | 7/2007 | Engel | G01F 1/7082 |
| | | | 73/861.44 |
| 7,263,874 B2* | 9/2007 | Fitch | G01N 11/16 |
| | | | 73/54.25 |
| 7,596,987 B2 | 10/2009 | Gysling et al. | |
| 7,604,054 B2 | 10/2009 | Hocking | |
| 2009/0114386 A1 | 5/2009 | Hartog et al. | |
| 2011/0088462 A1 | 4/2011 | Samson et al. | |
| 2012/0152024 A1* | 6/2012 | Johansen | E21B 47/123 |
| | | | 73/655 |
| 2012/0287749 A1* | 11/2012 | Kutlik | G01H 3/125 |
| | | | 367/7 |

FOREIGN PATENT DOCUMENTS

| | | |
|---|---|---|
| WO | WO-2010136809 A2 | 12/2010 |
| WO | WO-2010136810 A2 | 12/2010 |
| WO | WO-2012072981 A2 | 6/2012 |
| WO | WO-2012084997 A2 | 6/2012 |
| WO | WO-2012150463 A1 | 11/2012 |

OTHER PUBLICATIONS

Intellectual Property Office (UK), Search Report under Section 17(5) for Application No. GB1219797.6, dated Mar. 1, 2013.
International Searching Authority, European Patent Office, International Search Report for Application No. PCT/GB2013/052875, dated Jan. 31, 2014.
International Searching Authority, European Patent Office, Written Opinion for Application No. PCT/GB2013/052875, dated Jan. 31, 2014.
Optical Fiber Sensors: Advanced Techniques and Applications, Edited by Ginu Rajan, CRC Press, Taylor & Francis Group, Boca Raton, FL, 2015.

* cited by examiner

ACOUSTIC ILLUMINATION FOR FLOW-MONITORING

CROSS-REFERENCE TO RELATED APPLICATIONS

This application claims priority under 35. U.S.C. § 371 to Patent Cooperation Treaty Application No. PCT/GB2013/052875, filed Nov. 1, 2013, which claims the benefit of earlier-filed British Application No. GB 1219797.6, filed Nov. 2, 2012, the entire contents of which are incorporated herein by reference.

TECHNICAL FIELD

The present invention relates to a method and system which makes use of active acoustic illumination of fluid carrying structures such as boreholes, wells, pipes, and the like to allow for fluid flow monitoring or structural integrity monitoring to occur.

BACKGROUND TO THE INVENTION AND PRIOR ART

Optical fibre based distributed acoustic sensors (DAS) are known in the art. One high performance example is the iDAS™, available from Silixa Limited, of Elstree, UK. Further details of the operation of a suitable DAS are given in WO2010/0136809 and WO2010/136810, which also disclose that distributed acoustic sensors may be used for in-well applications, in that the acoustic noise profile can be used to measure the flow by noise logging at every location along the well. In addition, the noise spectrum can be used to identify the phase of the fluid.

However, one problem that arises in the use of DAS for flow monitoring is in fluid carrying structures where the flow is quiet, for example where the flow is substantially laminar, or with few eddies or other turbulent regions that cause noise. In such a case acoustic monitoring of the fluid carrying structure is unable to determine the fluid flow, or the fluid phase, due to the lack of input information into the sensor. Moreover, in fluid carrying structures where the flow is sometimes noisy and sometimes quiet, the monitoring of such structures with a DAS can result in large amounts of data, much of which is of little use when no noise is present.

Examples of flow carrying structures that are sometimes too quiet for conventional DAS monitoring are oil wells with low flow rates, and shale oil or shale gas wells. Even horizontal sections of piping can have quiet flow.

SUMMARY OF THE INVENTION

Embodiments of the present invention address the above problem by making use of a physical effect observed by the present applicants that noise, such as externally generated or internally generated noise, can be coupled into a fluid carrying structure such as a pipe, well, or borehole so as to artificially acoustically "illuminate" the pipe, well, or borehole, and allow fluid flow in the structure to be determined. In particular, in some embodiments of the invention acoustic energy is coupled into the structure being monitored at the same time as data logging required to undertake the monitoring is performed. The acoustic energy may have been deliberately created for the purpose of coupling into the structure, or it may have been created for another purpose, for example for seismic surveying, and is then also used for coupling into the structure by way of convenience. Alternatively, the acoustic energy may be incident noise that has not been specifically created for any purpose.

The coupling of acoustic energy into the structure has three effects, in that firstly the acoustic energy is coupled into the structure so as to "illuminate" acoustically the structure to allow data to be collected from which fluid flow or structural integrity may be determined, and secondly the amount of data that need be collected is reduced, as there is no need to log data when the structure is not being illuminated. Thirdly, there are signal processing advantages in having the data logging being undertaken only when the acoustic illumination occurs, in that any data averaging that needs to be performed is taken only over the (usually short) period of illumination. This can increase the signal to noise ratio considerably.

In view of the above, from one aspect there is provided a method of monitoring a fluid-flow carrying structure. The method comprises determining the generation of an acoustic wave; and at the same time as the generated acoustic wave is incident on the structure, sensing, using a distributed acoustic sensor, acoustic energy coupled into the fluid-flow carrying structure from the incident generated acoustic wave. Acoustic data corresponding to the sensed acoustic energy may then be stored, at least temporarily.

With the above, a "quiet" flow carrying structure may be deliberately illuminated by the generated acoustic wave, and acoustic data resulting from the illumination then sensed and stored for later use. By "determining", we simply mean noting that an acoustic wave is present that is capable of acoustically illuminating the structure. The acoustic wave may be deliberately created, either internally or externally to the structure, for the illumination purposes, or may be created for some other use, such as seismic surveying, its use for acoustic illumination then being a secondary beneficial effect. Alternatively, the acoustic illumination may be non-determinative, such as naturally, randomly or pseudo-randomly occurring incident noise from some other source.

In one embodiment the method calculates the speed of sound in one or more parts of the structure or in the fluid from the acoustic data. As such, embodiments of the invention may be used for both fluid phase determination, as well as structural integrity checking.

In another embodiment the stored or sensed data may be used to determine properties of fluid flow in the structure from the acoustic data. In one preferred embodiment the properties include the speed of fluid flow in the structure. As such, this embodiment may be used for fluid flow monitoring purpose.

For example, in one embodiment the method uses the stored acoustic data to calculate the speed of sound in the fluid from the acoustic data. In another embodiment the stored or sensed data may be used to calculate the speed of fluid flow in the structure from the acoustic data.

In one embodiment a processor is provided that is arranged to plot the acoustic data as a two dimensional space-time image. The processor then applies a two dimensional Fourier transform to the space-time image to obtain a transformed image. Gradients may then be identified in the transformed image, the identified gradients corresponding to the speed of sound, or at least a property or derivative thereof, of the coupled acoustic energy.

In one embodiment the identified gradients indicate the speed of sound in opposite directions along the flow carrying structure. This allows the processor to calculate the fluid flow in dependence on a difference between the respective speeds of sound in the fluid in the opposite directions.

In one embodiment the acoustic wave is generated remote from the structure, whereas in another embodiment the acoustic wave may be generated next to or within the structure.

In one embodiment the acoustic wave is generated by a seismic source, wherein preferably the seismic source is a source selected from the group comprising: airguns, vibroseis, explosives, or piezo transducers.

In another embodiment the acoustic wave is generated by an internal source to the structure. In particular the acoustic source may be a mechanism driven by the fluid flow.

The acoustic wave may take many forms, and may be for example one of a pseudo random sequence or an impulse.

In a preferred embodiment acoustic data is not stored substantially during time periods between the periods when the acoustic wave is incident on and propagating through the structure. This reduces the amount of data that is generated and stored by the DAS.

In one embodiment the generation of the acoustic wave and the sensing and storing of acoustic data are synchronised. In particular, the generation of the acoustic wave may be triggered, and then the DAS may wait for any propagation delay until the generated wave is incident on the structure before sensing the coupled acoustic energy and storing corresponding acoustic data.

In the above embodiment the DAS preferably ceases the storing of acoustic data once the acoustic wave has propagated along the structure.

In a particularly preferred embodiment the distributed acoustic sensor is an optical fibre based sensor. Moreover, preferably the structure is a pipe, well, or borehole.

From a further aspect the present invention also provides a system for monitoring a fluid-flow carrying structure, the system comprising an acoustic generator for generating an acoustic wave; and a distributed acoustic sensor for sensing, at the same time as the generated acoustic wave is incident on the structure, acoustic energy coupled into the fluid-flow carrying structure from the incident generated acoustic wave and for storing acoustic data corresponding to the sensed acoustic energy.

In another aspect the present invention also provides a fluid-flow carrying structure comprising an elongate fluid carrying channel through which fluid may flow; and an acoustic transmission mechanism arranged in use to couple incident acoustic energy into the fluid flow carrying structure. In this aspect the fluid flow carrying structure may be specially adapted to allow illuminating acoustic energy incident from the outside to be coupled therein, thereby enhancing the acoustic illumination effect of the present invention.

In one embodiment the acoustic transmission mechanism comprises a drum structure having a first surface and a second surface and an acoustic connection mechanism to conduct acoustic energy incident on the first surface to the second surface. The first surface is reactive to incident acoustic waves and vibrates when such waves are incident thereon. The acoustic vibrations are passed by the acoustic connection mechanism (such as one or more linking arms or the like) to the second surface, which is arranged to radiate the acoustic energy outwards, into the structure, and thereby couple the energy into the structure.

In another embodiment the acoustic transmission mechanism comprises an acoustic transmission rod extending through at least one part of the structure for transmitting acoustic energy through the at least one part. In this case incident acoustic vibrations are passed by the rod into the structure, and thereby coupled into the structure.

In some embodiments the structure is a pipe, well, or borehole, and particularly an oil or gas well.

Further features and aspects of the invention will be apparent from the appended claims.

BRIEF DESCRIPTION OF THE DRAWINGS

Further features and advantages of the present invention will become apparent from the following description of an embodiment thereof, presented by way of example only, and by reference to the drawings, wherein like reference numerals refer to like parts, and wherein.

DESCRIPTION OF THE EMBODIMENTS

Overview of Embodiments

The success of DAS-based fluid flow measurements depends on the presence of audio frequency and sub-audio frequency noise within the flow. Quiet flows have been seen not to produce useful DAS generated data, such as, for example, k-omega (k-ω) data. Ambient noise from the ground surrounding boreholes can 'creep in' to pipes to illuminate them acoustically, but naturally generated ambient levels are usually much too low to be detectable by a DAS. To solve this problem embodiments of the invention combine a sound source in synchronization with monitoring using a DAS, so that the sound source acoustically illuminates the interior of the borehole, and allows the DAS to log data that can be used to determine the fluid flow.

Determination of Fluid Flow

Figure 1:
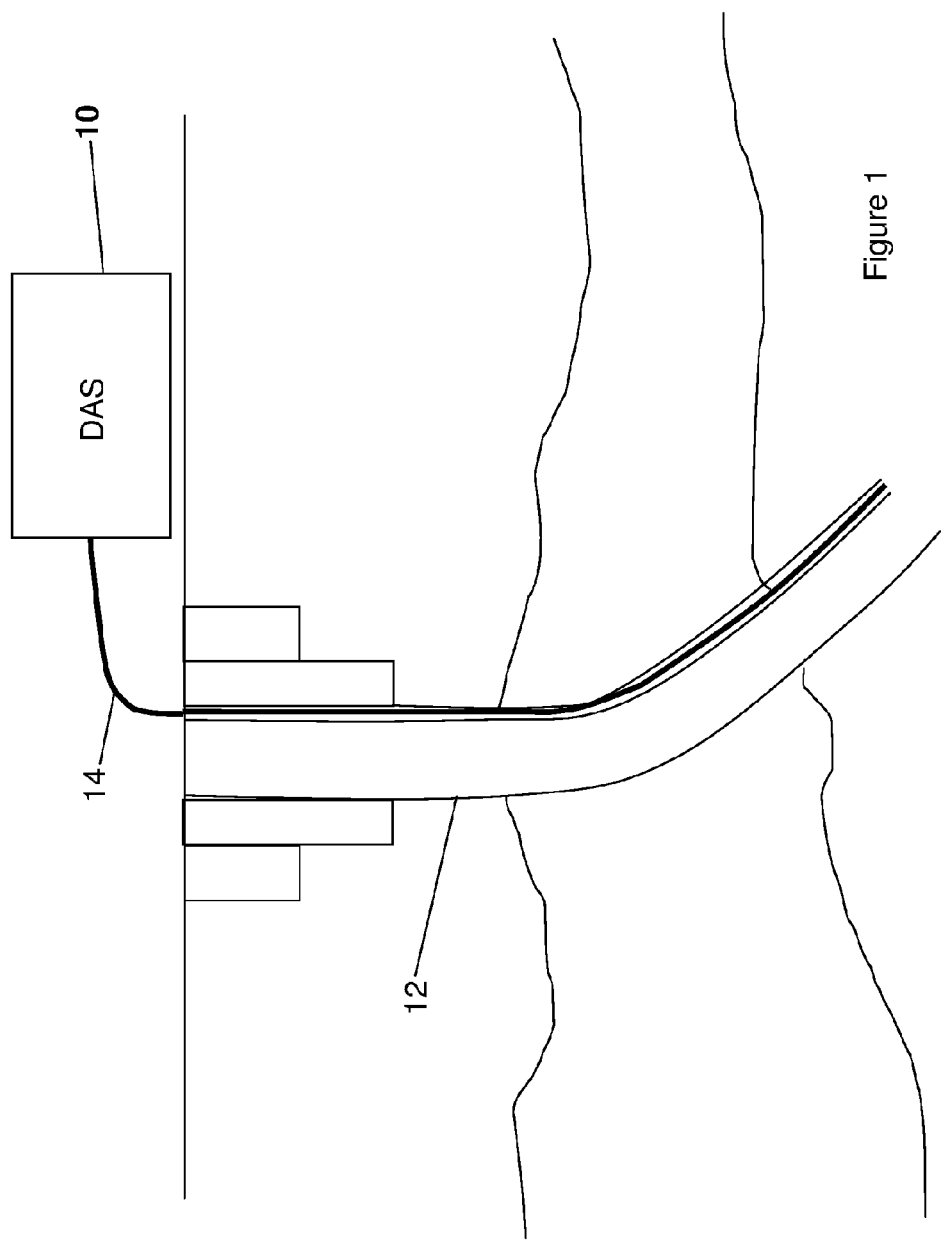
FIG. 1 is a diagram illustrating an example DAS deployment of the prior art.

FIG. 1 illustrates a typical DAS deployment in an oil well. The well 12 extends through rock strata as shown, and a fibre optic cable 14 is provided running along the length of the well, in this case substantially parallel thereto. In other embodiments the cable may extend along the well in a different manner, for example wrapped around elements of the well. In this respect, all that is important is that there is a known relationship between the different parts of the cable and the different parts of the well.

Figure 2:
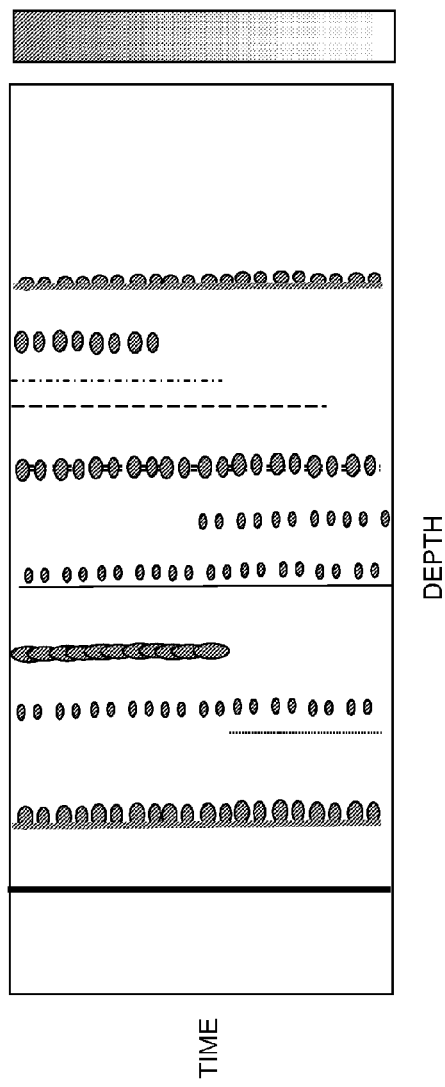
FIG. 2 is a drawing of an example space-time plot of the data collected by a DAS in a deployment like that of FIG. 1.

The fibre optic cable 14 is connected to a distributed acoustic sensor (DAS), such as the Silixa Ltd iDAS™, referenced previously. The DAS is able to record sound incident on the cable at between 1 m and 5 m resolution along the whole length of the cable, at frequencies up to around 100 kHz. Hence, monitoring of the well with the DAS results in a large amount of data, that may be represented by a two dimensional space-time plot, an example of which is shown in FIG. 2. Here, the horizontal axis shows "depth", or distance along the cable, and the left hand vertical axis shows time. The right hand vertical axis shows a colour chart, with different colours representing sound of different intensity. Hence, the 2D space time plot provides a visual record of where on the cable sound was heard, and at what measurement time.

Figure 3:
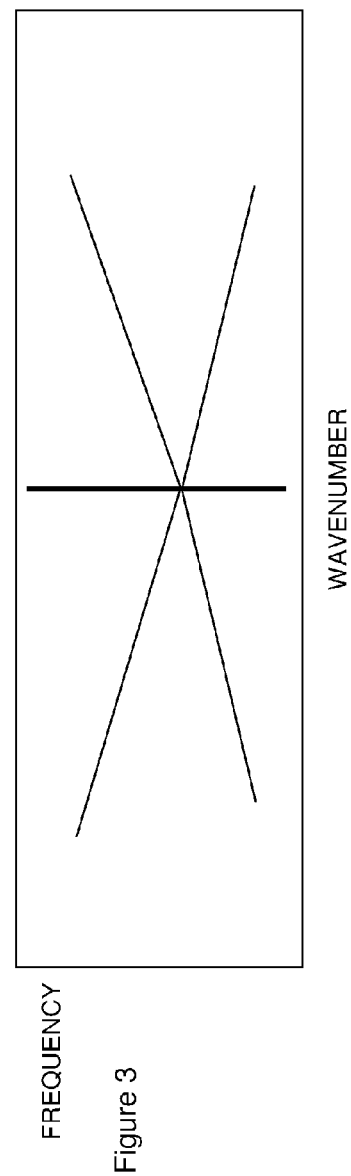
FIG. 3 is a drawing of a 2D Fourier transform (kω plot) of the space-time plot of FIG. 2.

In more detail, the DAS system can measure the phase of the acoustic signal coherently along the fibre optic cable. Therefore, it is possible to use a variety of methods to identify the presence of propagating acoustic waves. In one such method, described solely by way of non-limiting example, digital signal processing can transform the time and linear space (along the well) into a diagram showing frequency ($\omega$) and wavenumber (k) in k-$\omega$ space. A frequency independent speed of sound propagation along the well will show up as a line in k-$\omega$ space. FIG. 2 shows the time and space signal and FIG. 3 shows the corresponding k-$\omega$ space. Using the data in FIG. 3, a good fit for the speed of sound can be calculated, by determining the gradient of the diagonal lines. The frequency band over which the speed of sound can be determined is more than sufficient for compositional and flow characterization. With the DAS system the speed of sound can be evaluated over a large section of the well and, therefore, measure the distributed variations of the flow composition and characteristics along the well. The technique is particularly powerful for determining the composition of the flow—for example, gas has a speed of sound of around 600 m/s whereas water has a speed of sounds around 1500 m/s.

Figure 4:
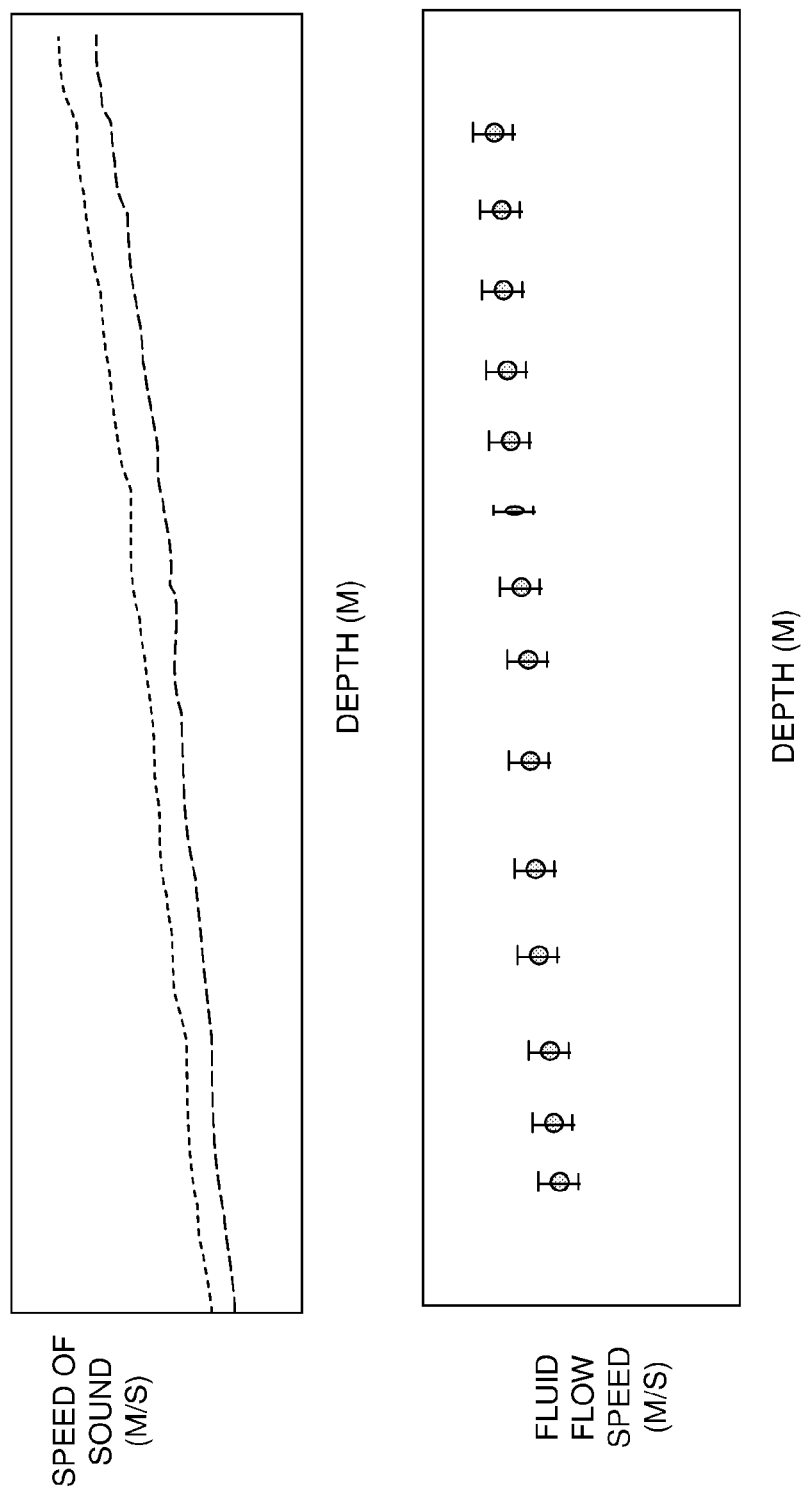
FIG. 4 is a graph showing upwards and downwards speed of sounds in a pipe, (top) together with calculated Doppler shifts (bottom) that provide fluid velocity measurements.

Using such k-$\omega$ analysis the speed of sound can also be determined throughout the entire length of the well. Importantly, each of the two diagonal lines shown in the k-$\omega$ space of FIG. 3 corresponds to the speed of sound either travelling up or down the well. These two lines can be analysed to reveal the Doppler-shifted sound speeds for upward and downward propagating sound within the fluid of interest. FIG. 4 shows the distributed flow determined in a gas injector based on Doppler shift measurements for a 30 s sampling. The determined flow speed varies with depth in the well corresponding to the change in hydrostatic pressure for a section of tubing with a uniform inner dimension and a gradually sloped well trajectory. In total the instantaneous and locally determined flow is roughly within +/−0.3 m/s (that for this well is 10%) of the actual flow speed. The match to reference measurements is within the uncertainties of an instantaneous measurement, the fluid property and the distribution of the pressure drop within the well.

In further detail, it is possible to estimate the speed of a given flow by monitoring the speeds of sound within that flow. In this analysis, it is assumed that the flow direction is coincident with the array layout (e.g. the direction of arrival for acoustic signals is known to be 0 or 180 degrees). The main principle used is that any sound contained within the flow reaches each consecutive sensor with a certain delay. Knowledge of the spatial sampling (i.e. the distribution of the cable along the well) can be used to calculate speed of sound by taking the ratio of average inter-sensor time difference of arrival and the average spatial distance between sensors. This operation can be easily done in the frequency domain. To perform this operation, in one embodiment one constructs a space-time plot of the signal across a neighbourhood of sensors. The 2D Fourier Transform of information this will give a wavenumber-frequency (k-$\omega$) plot.

If the speed of sound is constant across all frequencies (i.e. there is no dispersion) then each frequency ($\omega$) of a signal will correspond to a certain wavenumber (k) on the k-$\omega$ plot. Thus ideally a space-time signal will be mapped into a single straight line on the k-$\omega$ plot. From the wave equation we know that kc=w, where c is the speed of sound. So estimating the slope of the line of highest energy on the k-$\omega$ plot will give us the speed of sound in the medium.

Since the waveguide can sustain propagation both along and against the direction of flow, the k-$\omega$ plot can show two slopes for each mode of propagation: one positive and one negative. As the slope of each of these lines indicates the sound speed in each direction, the Doppler method can be used to derive the speed of sound from the 2D FFT according to the well-known method of analysis below.

c+=c+v [speed of sound along the flow]
c−=c−v [speed of sound against the flow]

c+ and c− are found as slopes on a k-$\omega$ plot. Combination of the two equations above gives the flow speed (Ev[1]) as v=(c+−c−)/2.

Please note that whilst the above description makes use of processing using k-$\omega$ plots, in other embodiments different processing may be undertaken to achieve the same results, and not all embodiments of the invention are required to use the k-$\omega$ techniques described.

Illumination Using Noise Sources

As noted above, embodiments of the invention are directed at determining fluid flow of quiet wells, by using an acoustic source to "illuminate" the well and allow the DAS to collect data from which the fluid flow can then be found. It is therefore necessary to consider the physical mechanism of how acoustic energy can be coupled into a fluid carrying structure such as a pipe, well, or borehole.

Waveguides are systems which exhibit a very high propensity to direct energy along particular pathways. Pipes are one-dimensional acoustic waveguides, the acoustic characteristics of which have been well-analysed within the classical acoustics literature. As a result of these waveguide properties, acoustic sources external to pipes can be used to illuminate acoustically the internal volumes of those pipes even when the source of interest is external to the pipe. In one embodiment of the present invention, a source in the vicinity of the pipe, such as a vibroseis or dropped weight, will drive an acoustic signal into the ground. As the signal radiates through the ground and encounters the pipe, acoustic energy will tend to be coupled into the pipe and be redirected along the pipe primary dimension. An acoustic sensor array mounted within or along the pipe coincident with the pipe principal dimension can be used to interpret the speed of sound within the pipe volume and wall (and, if present, the outer annulus). Regardless of the relative phase of different acoustic waves as they enter the pipe, the speeds of sound in both the forward and reverse directions of propagation can be determined, and hence flow speed can be observed. One aspect is that the energy entering the pipe should preferably be below the cutoff frequency for the waveguide, else energy will not propagate as a plane wave and wave speed determination will be increased in complexity.

Potential Noise Sources

Figure 8:
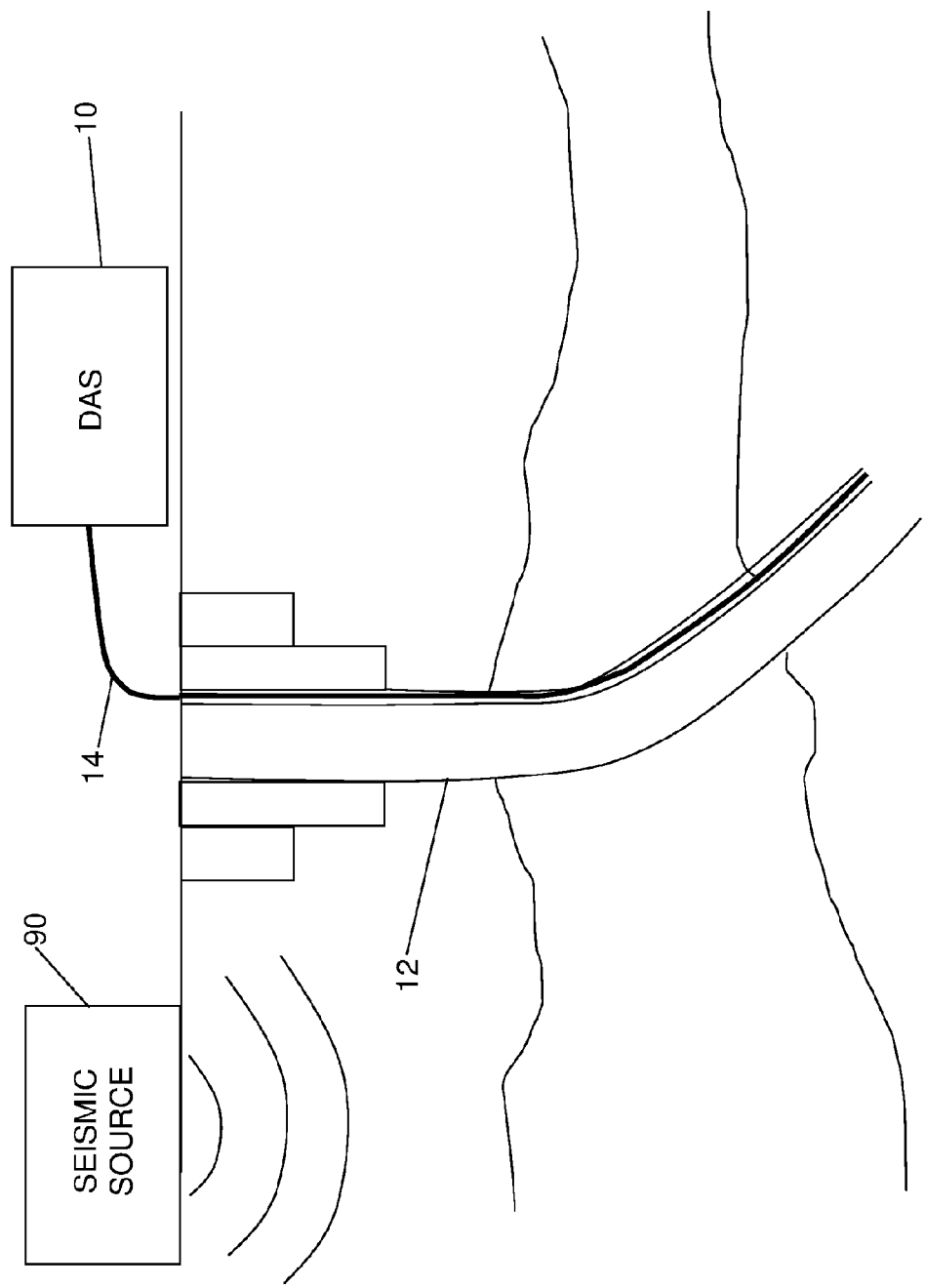
FIGS. 8 to 10 are diagrams illustrating how various noise sources may be provided in embodiments of the invention.
Figure 9:
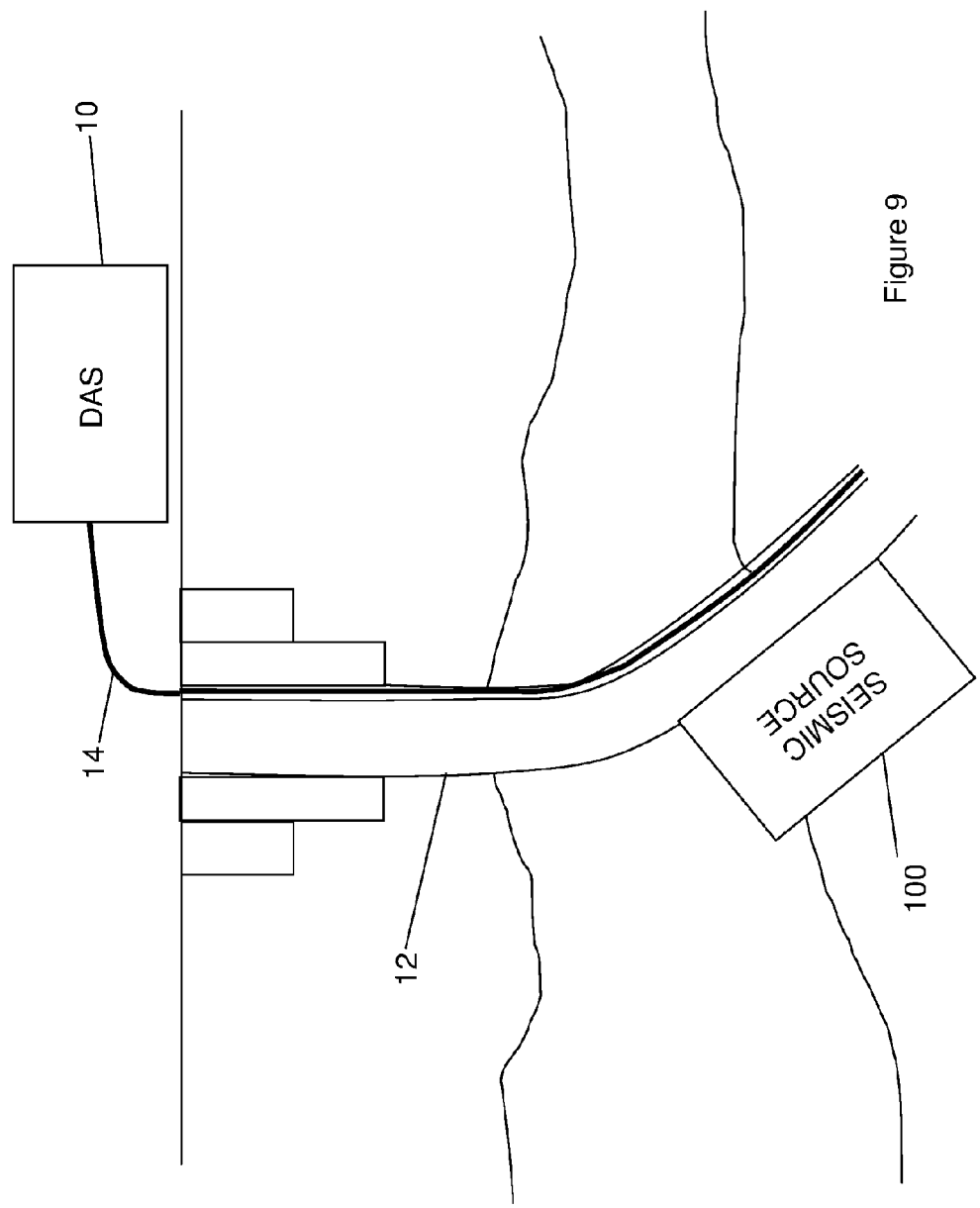
Figure 10:
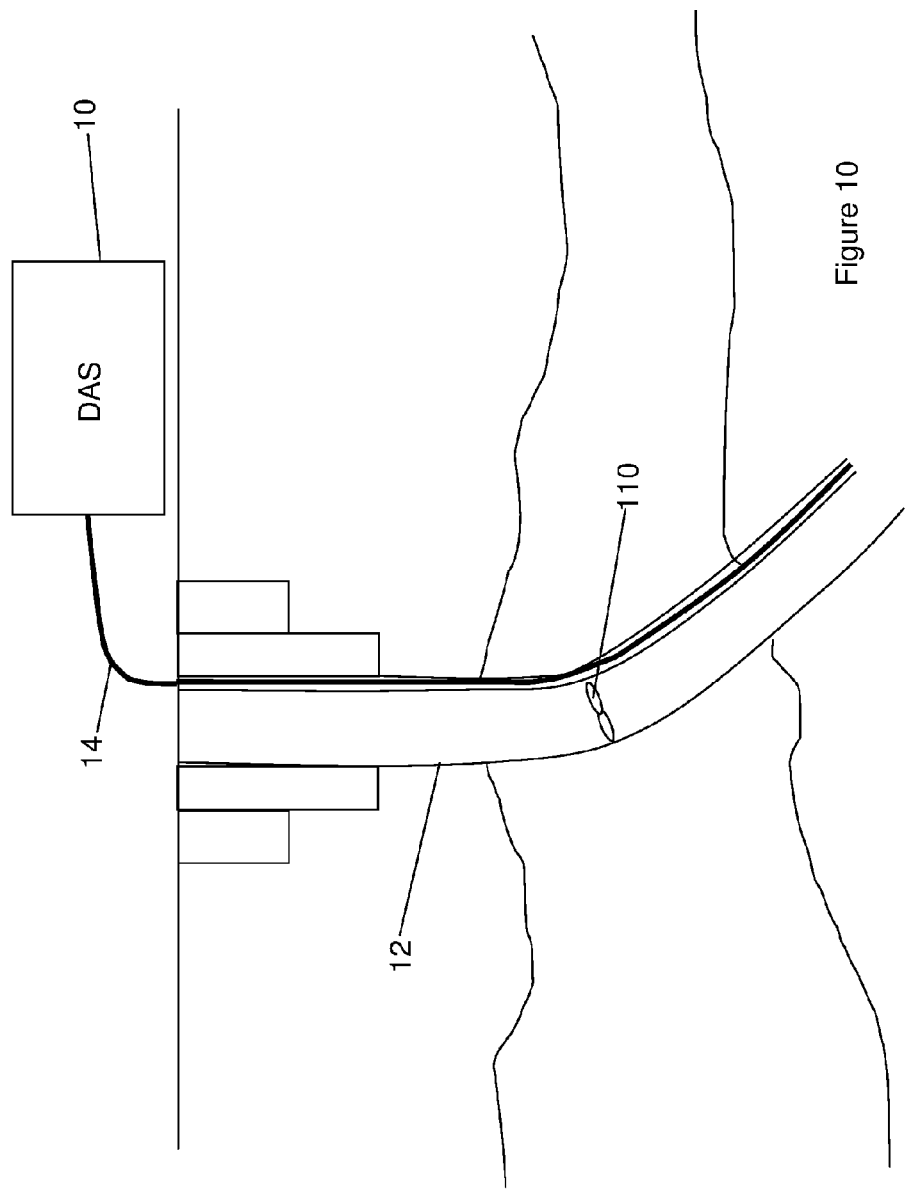

Many different noise sources may be used in embodiments of the invention, as shown in FIGS. 8 to 10. For example, seismic sources such as seismic source 90 remote from the well, as shown in FIG. 8, or next to or in the well, as shown in FIG. 9, may be used. 1. Such seismic sources (90, 100) may be airguns, vibroseis, explosives, or piezo transducers either placed outside the well or in the well.

In addition, passive sources powered by the flow, for example a clapper or a spinner 110 with a clicking mechanism attached may be used, as shown in FIG. 10.

Additionally, in further embodiments active sources powered by power harvesting techniques may be used. An example is that the flow or vibrations in the well may be used to generate power which is then used to power a device (for example a pulsing piezo).

In further embodiments pump noise may be used, or, for offshore wells, the noise from boats or ships located near the base well or pipe may be used. In addition, pressure waves from opening and closing valves within a well or pipe may be used, in that the opening and closing, if performed suddenly enough, can generate an acoustic pressure wave that travels along a pipe or well of which the valves form a part.

Moreover, in some embodiments acoustic sources can distributed along the well, borehole, or pipe. For example, the distribution may be regular, in that the sources are evenly spaced along sections of the well, borehole, or pipe, or the distribution may follow a mathematical function. For example, the distribution might be logarithmically spaced along one or more sections of a pipe. In other embodiments, acoustic sources might be randomly or pseudo-randomly spaced along the pipe. Moreover, in further embodiments different sections of pipe may have a different distribution of acoustic sources therein.

With respect to the precise noise signal that may be used, the use of random or pseudo-random vibroseis-generated signals in a zero-offset arrangement tandem with a flowing well monitored by a DAS should allow for sufficient averaging to yield useful flow data even in nearly silent wells. Noise generated within wells could also be used for this type of illumination.

In practice, this would involve bringing a vibroseis up to a well, and driving it with a pseudo-random signal for a while (maybe a few minutes) while the DAS acquires data. This could also be done with other excitations (single pulses, chirps) but pseudo-random is practically and theoretically the most robust method.

Method of Operation

Figure 11:
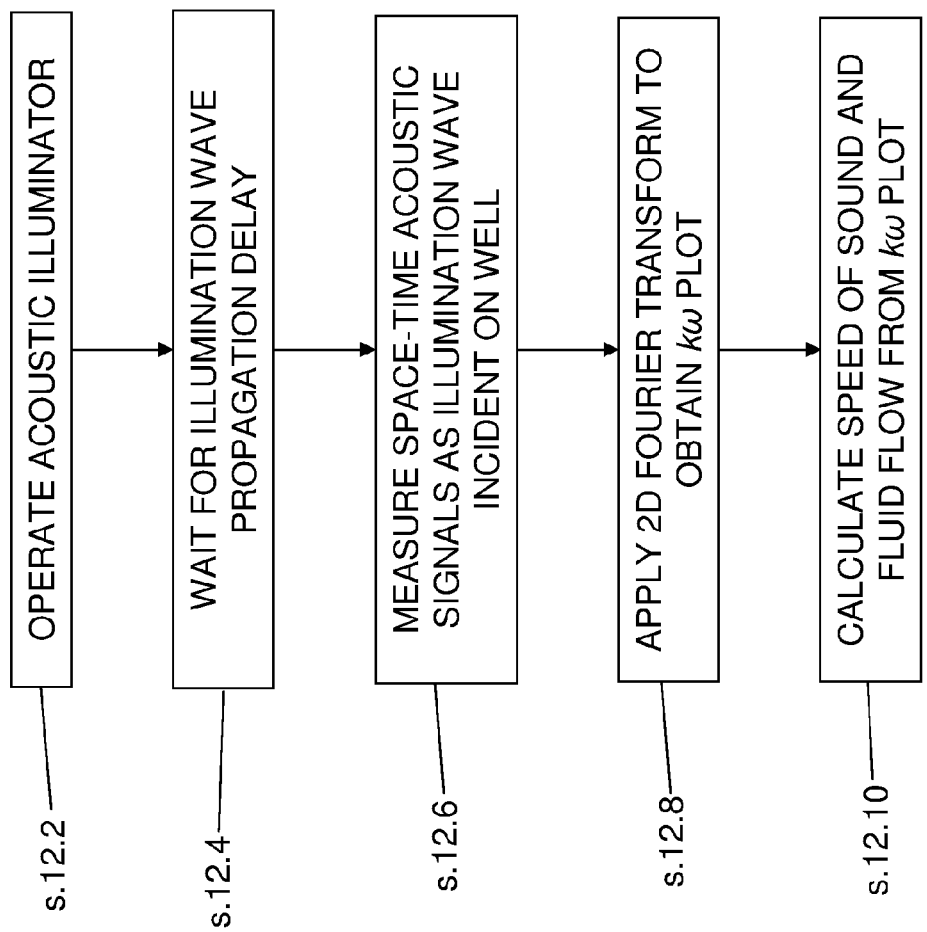
FIG. 11 is a flow diagram illustrating the sequence of operations in embodiments of the invention.

FIG. 11 illustrates the overall operation of the embodiments in FIGS. 8 to 10. At step 12.2 the acoustic illuminator (i.e. the sound source, whether seismic or otherwise) is operated. If the sound source is some (known) distance away then it is necessary to wait for the illumination acoustic wave to propagate to the site of the well, pipe, or borehole, as shown at step 12.4. However, if the sound source is local, then it is not necessary to wait for this propagation period.

At the same time as (or just before) the acoustic wave is incident on the well, pipe, or borehole, the DAS system 10 is activated to begin logging space-time acoustic data, at step 12.6. Thus, the DAS begins to record acoustic data representative of the incident acoustic wave being coupled into the fluid carrying structure. Once the acoustic energy has been coupled into the structure and propagated there along, the data logging can then stop. Hence, it becomes necessary to log data for only a short period of time during the actual illumination by the acoustic source.

Once the space time data has been obtained, at steps 12.8 and 12.10 the same steps as described above to calculate the speed of sound in the flowing medium, and then the actual flow speed itself are performed. These steps may be performed substantially in real time immediately after the data has been captured, or as a post-processing step some time later.

One benefit to using active acoustic illumination in fluid flow metering in boreholes is the ability to synchronize the flow measurement with the acoustic source firing. This can greatly increase the signal to noise ratio of results by allowing averaging to be calculated using only data known to contain useful acoustic signal. Quiet periods outside of the time when an acoustic illumination signal is present are not recorded and hence do not contribute to the averaged signal. This method also allows for a significant reduction in the amount of data that needs to be collected since the period of acoustic illumination represents only a fraction of the recording time when compared to continuous data logging.

Figure 5:
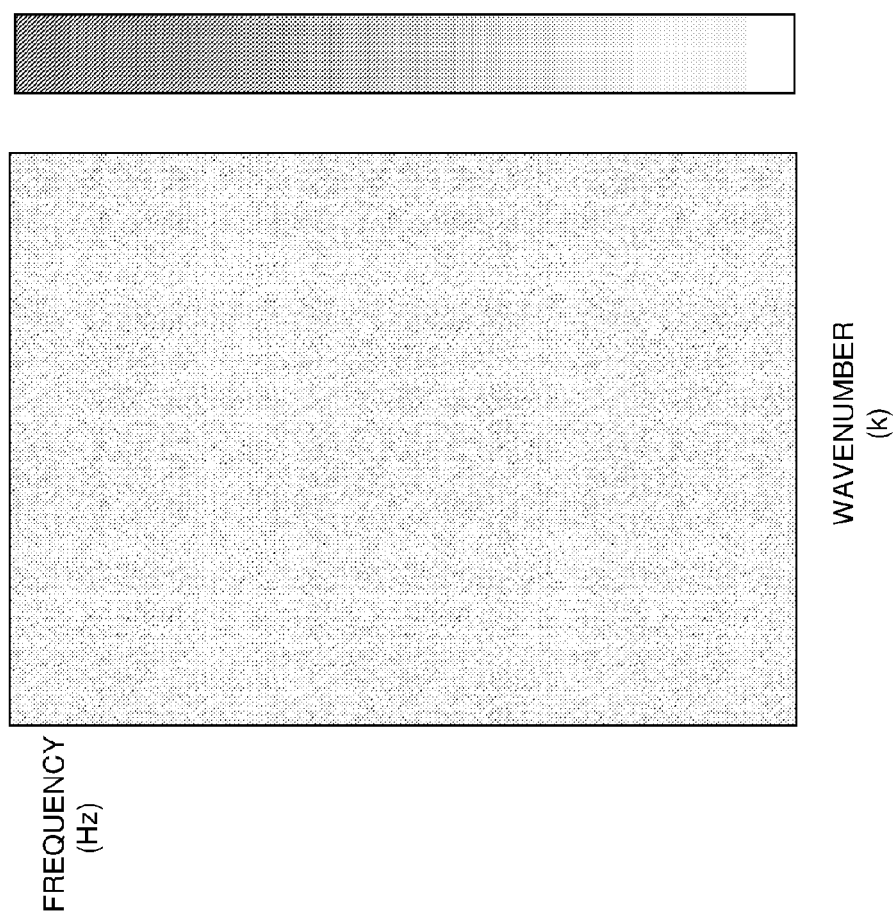
FIGS. 5 to 7 are drawings of example kω plots taken at different times in the same well subject to acoustic illumination (which occurs in FIG. 6)
Figure 6:
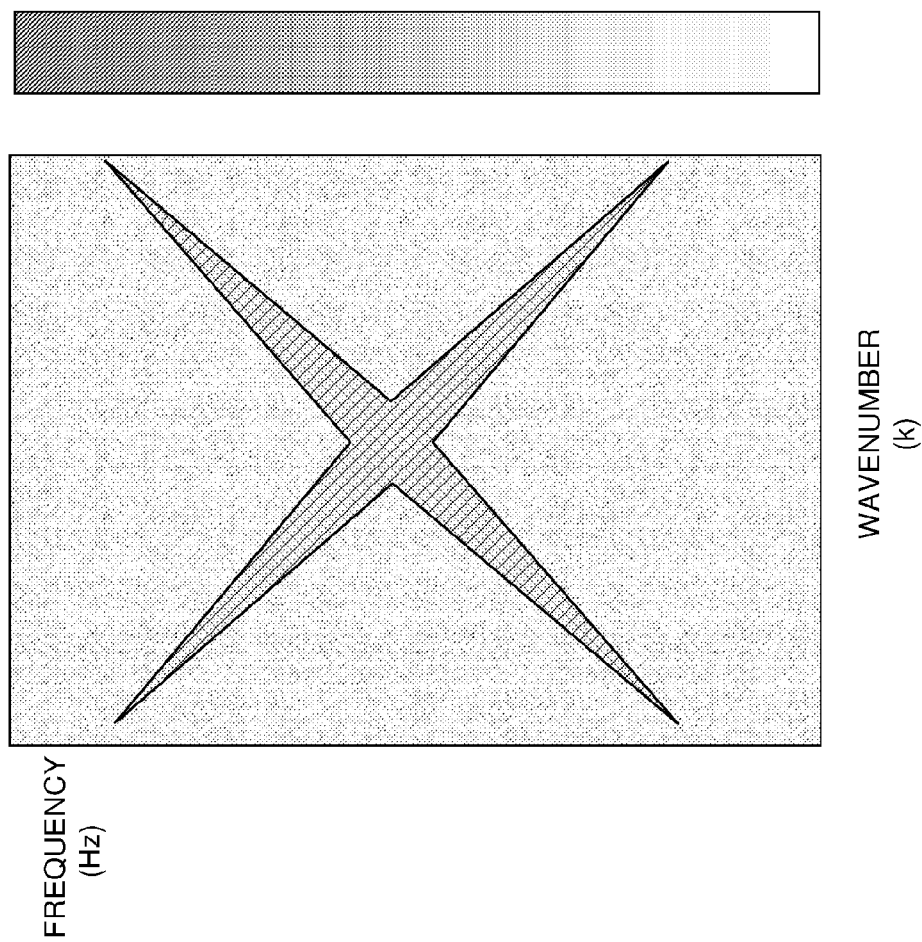
Figure 7:
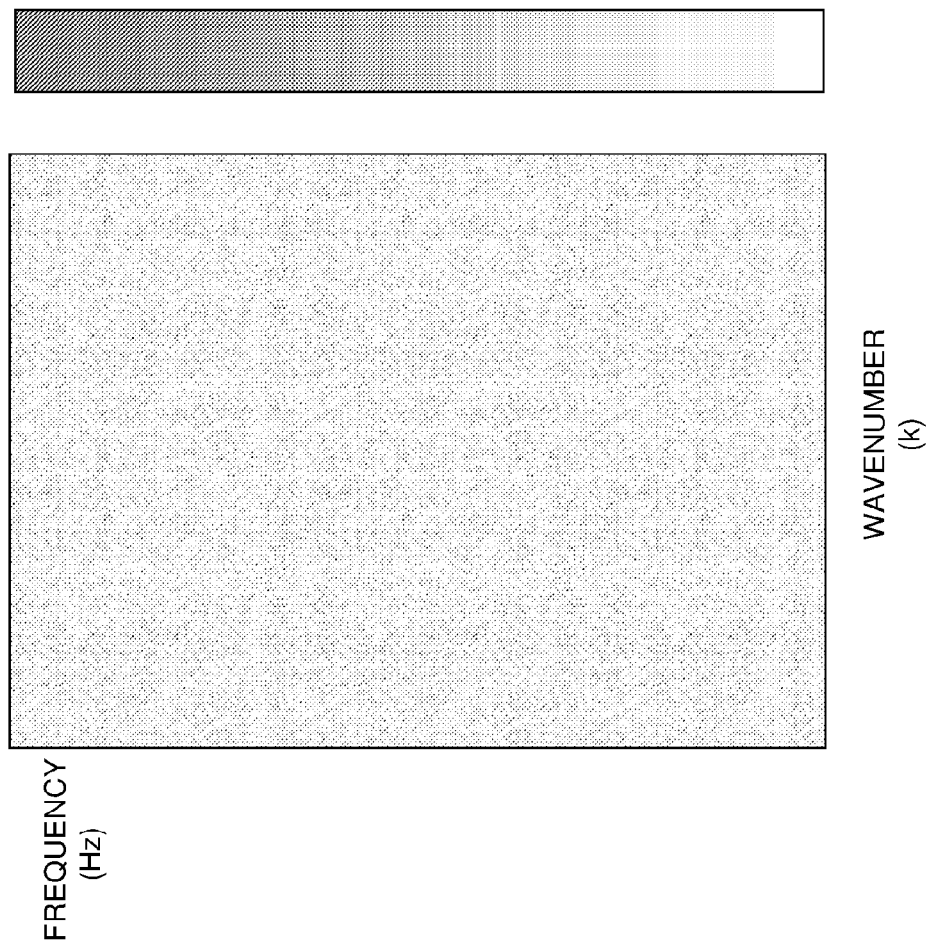

For this to be done effectively it is necessary to synchronize the acoustic source generation with the recording made by the DAS. In embodiments of the invention this can be done in two ways. The first method uses an accurately timed trigger signal to initiate the acoustic source and the DAS data recording at the same time. Depending on the position of the acoustic source used to provide the illumination relative to the borehole, delays can be built into the recording start time to allow for the travel time of the acoustic waves to the borehole or a specific region of the borehole. For each source firing a short recording is made and the flow speed calculated, in between source firings data does not need to be collected. The second method fires the source at regular intervals synchronized to an accurate clock signal such as GPS time. The DAS, which must also be synchronized to the same clock, records at the same intervals or offset by a certain amount of time to allow for travel time of the acoustic illumination source signal Results Example results provided by an embodiment of the invention are shown in FIGS. 5 to 7, which show k-ω) plots for a number of discrete times during an experiment. In this experiment, an otherwise quiet pipe with fluid flowing therein pipe was struck with a hammer to provide an acoustic impulse. When k-ω plots are made in the absence of any acoustic illumination (as shown in FIGS. 5, and 7), the speed of sound cannot be seen. However, when k-ω plots are made during time periods coincident with the impulse (corresponding to FIG. 6), the speeds of sound corresponding to the various media within the pipe cross-section can be seen. As described above, these speeds of sound can be used to derive (1) the flow speed (2) information concerning the nature of the fluid and (3) well integrity data.

As noted, FIGS. 5 to 7 show k-ω results are shown for a cement-lined pipe with a dense acoustic sensor array embedded within the array.

| FIG. Number | Time period | Condition | Summary of kω plot |
|---|---|---|---|
| 5 | 0 s-0.15 | Silence | No speeds visible |
| 6 | 0.20 s-0.35 s | Impulse introduced by hammer on pipe exterior | Waveguide characteristics including fluid sound speed clearly visible |
| 7 | 0.40 s-0.55 s | Silence | No speeds visible |

In summary, therefore, embodiments of the present invention provide for the deliberate incidence of an actively generated acoustic wave onto a fluid flow carrying structure simultaneous with data logging being undertaken by a DAS that monitors the structure. The incident acoustic energy couples into the fluid flow carrying structure and effectively acoustically propagates along the fluid, allowing speed of sound in the fluid to be determined, from which fluid flow speed can then be determined. Many different sound sources either within or without the fluid flow carrying structure may be used, such as seismic sources, or flow driven devices.

Figure 12:
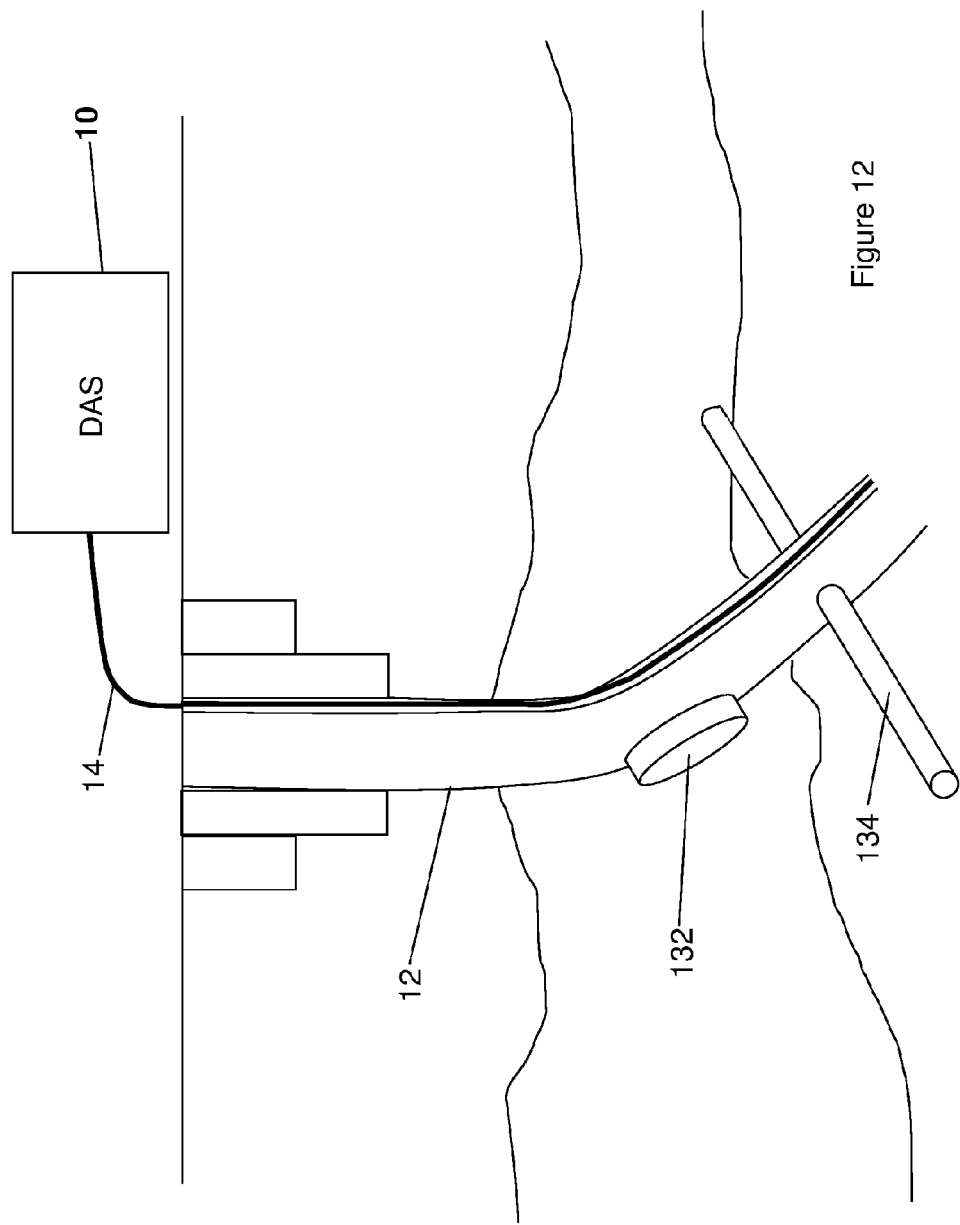
FIG. 12 is a drawing illustrating possible modifications to be made to casing of a well to allow the well to be more acoustically coupled to the surroundings.
Figure 13:
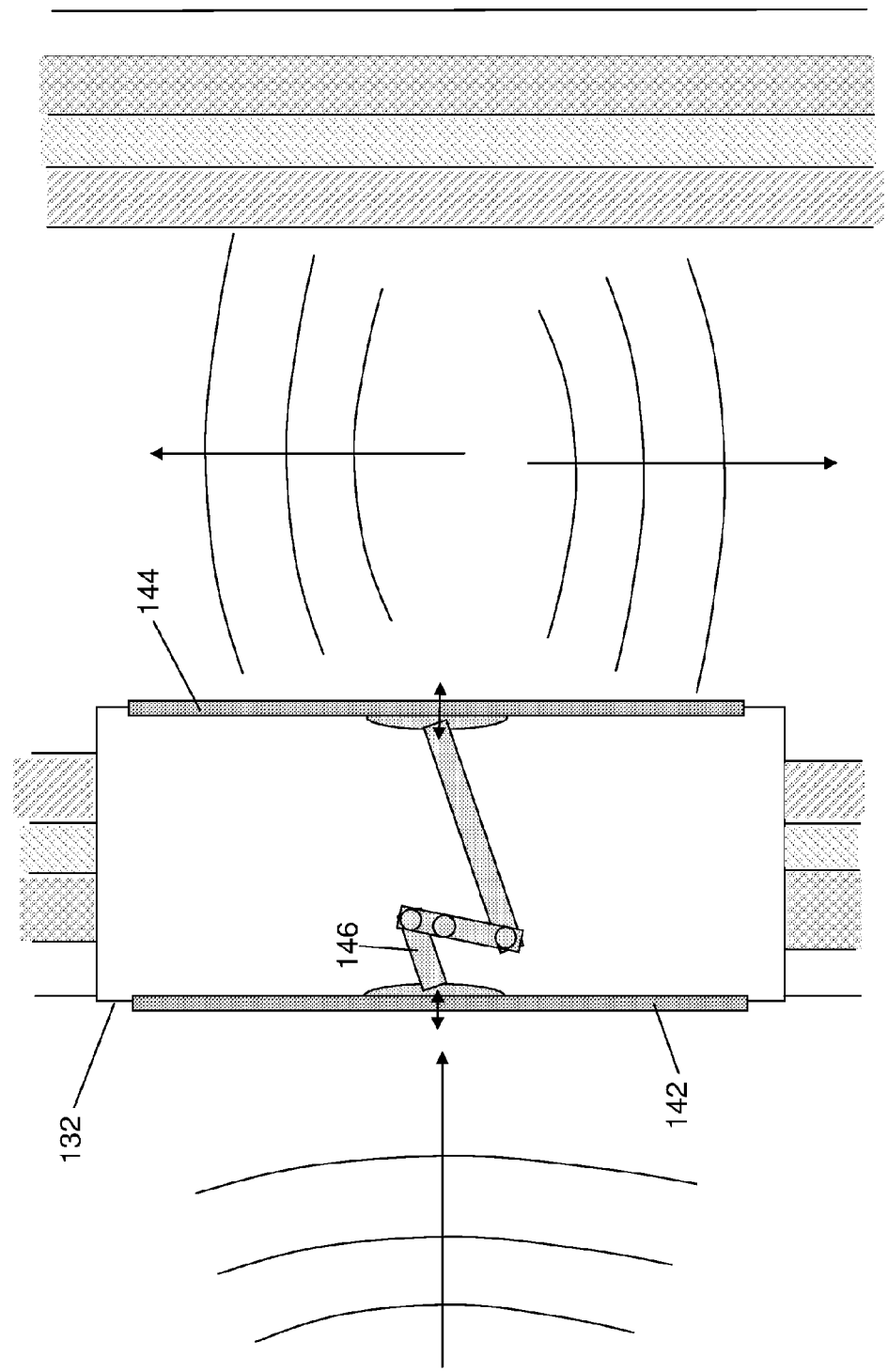
FIG. 13 is a drawing illustrating one of the modifications of FIG. 12 in more detail.
Figure 14:
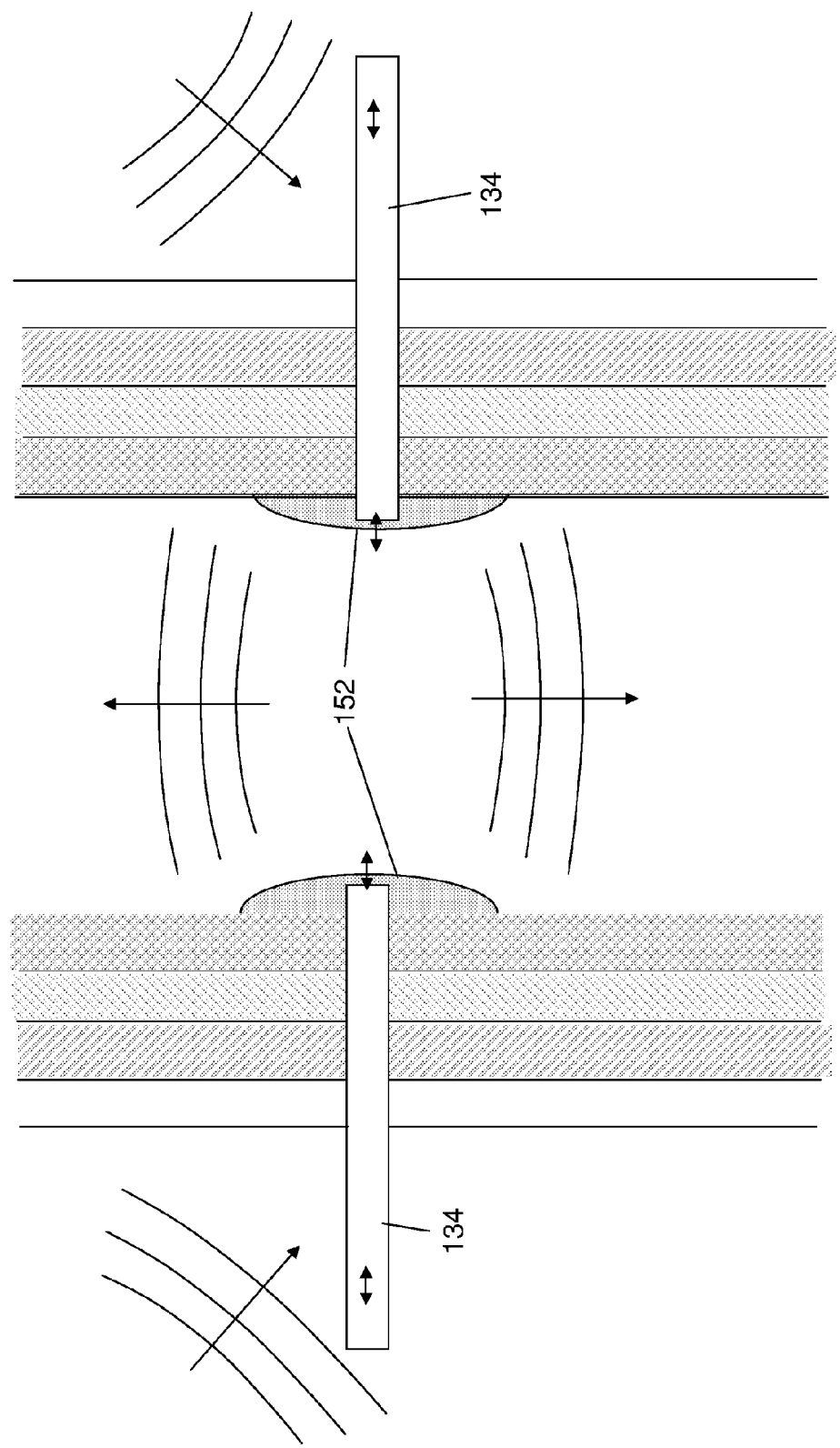
FIG. 14 is a drawing illustrating another of the modifications of FIG. 12 in more detail.

A further aspect of the present invention relates to the adaptation of the fluid flow carrying structure itself so as to enhance its ability to couple into its interior acoustic energy incident from the outside. In this respect external acoustic illumination of the interior of the structure can be enhanced by coupling into the structure more of the incident energy. Thus, for example, in the case of an oil or gas well the outer casing of the well may be adapted by the provision of an acoustic coupling mechanism arranged to couple into the interior of the well acoustic energy incident externally. FIGS. 12 to 14 illustrate specific examples.

As shown in FIG. 12, the outer casing of a well 12 may be provided with devices or other adaptations to improve the ability of the well to couple into its interior incident acoustic energy, that then travels along the well in waveguide mode, as described previously. In particular, one such mechanism is a drum type arrangement 132 which passes from the outside of the well through the outer cement and casing, into the interior, and which operates similar to an ear drum to transmit acoustic energy. FIG. 13 illustrates the arrangement in further detail.

More specifically, in FIG. 13 an acoustic transmission drum 132 is shown, wherein the drum extends in this case through (in order from outside in the direction inwards) the cement, casing, annulus, and tubing into the interior of the well. In other embodiments the drum may only extend through a subset of these layers, for example, may extend through the cement or casing into, but not through, the annulus, or through the tubing and annulus from the casing. In further embodiments individual drums 132 may be provided in the respective layers, or a subset of the layers of the well. For example, the tubing layer may be provided with a respective drum that passes therethrough, and the casing layer may be provided with a respective drum that passes therethrough. Others of the layers may also be provided with their own respective drums. In some embodiments, where one or more drums per layer are provided, the drums may preferably be in spatial alignment from layer to layer, such that acoustic energy may be passed from drum to drum.

An acoustic transmission drum 132 is shown in more detail in FIG. 13. The drum includes a first acoustically reactive surface 142, such as a membrane or the like, which is sensitive to incoming acoustic vibrations such that the vibrations are transferred into the membrane. A second acoustically reactive surface 144, which may also be a membrane, is mechanically coupled to the first surface such that any acoustic vibrations induced in the first surface are transferred to the second surface. In this respect, the mechanical coupling 146 may be arranged to amplify the acoustic vibrations transferred to the second surface, for example by using a linked arm arrangement with a pivot point arranged to provide a mechanical advantage. In particular, as shown in FIG. 13, a first arm attached at one end to the first surface 142 is pivotally attached to a linking arm. The linking arm is pivotally mounted about a fixed pivot point, and is pivotally attached at its other end to one end of a second arm. The second arm is attached at its other end to the second surface 144. The position of the fixed pivot can be set such that the acoustic vibrations transferred from first surface to the second surface are increased or decreased in amplitude.

Other transfer mechanisms may be used. For example, a straight-arm linkage (i.e. without the pivots) may be made between the two surfaces, so that vibrations in the first surface are directly transferred to the second surface. Such a linkage may simply comprise a connecting rod connecting the inner surfaces of the two surfaces.

In the embodiment of FIG. 13, the outer face of second surface 144 is located within the main body of the well, in direct contact with any fluid flowing therethrough. Therefore, acoustic vibrations can be transferred directly into the fluid, to then propagate up and down the fluid carrying structure, as described previously, and as shown.

The operation of the arrangement is as follows. External acoustic vibrations incident on the first surface are transferred to the first surface, and then, via the linkage mechanism, to the second surface. The acoustic vibration of the second surface is then coupled into the fluid in the structure, and propagates up and down the structure as if the structure were a waveguide, as described previously.

A second acoustic coupling mechanism is shown in FIGS. 12 and 14. This mechanism comprises rods 134 which extend from the casing through the cement layer and into the surrounding rock strata. On FIG. 12 the rods are not shown to scale, and as an example may be a few (2-3) to several (20-30) centimeters in length, although other lengths may be used. As shown in FIG. 14, the rods are coupled through the cement, casing, annulus and tubing into the well interior, and are provided on their inner ends with vibration surfaces 152 to transmit any acoustic vibrations in the rods into the fluid in the well. The rods may be firmly mounted such that they cannot move, or alternatively may be slightly sprung mounted (not shown), such that they are able to move in and out in their elongate direction, as shown in FIG. 14.

The operation of the arrangement of FIG. 14 is as follows. External acoustic vibrations in the surrounding rock strata and incident on the rods are transferred to the through the rods into the interior of the structure, and via the vibration surfaces into the fluid flowing therethrough. The acoustic vibration of vibration surfaces is coupled into the fluid in the structure, and propagates up and down the structure as if the structure were a waveguide, as described previously.

In variations of the embodiment of FIG. 14, the rods may only extend through some of the outer layers, such as the cement layer and the casing for example, but not through all of the outer layers.

In the above embodiments focus has been made on coupling acoustic illumination energy into the fluid in a structure so as to illuminate the fluid and allow fluid flow to be found. However, in further embodiments the acoustic illumination energy may be intentionally coupled into the structure itself, to allow speed of sound in the structure to be determined to allow for structure integrity checking. For example, in the case of an oil well acoustic energy may be coupled into the cement layer and detected propagating through the cement layer to determine cracks or discontinuities in the cement layer. In this respect, the cement layer may be provided with an acoustic coupling mechanism such as those described above, which ends within the cement layer, and goes no further into the structure. For example a rod 134 or drum 132 may be provided extending from outside the well into the cement layer, but no other layer. This would act to couple incident acoustic energy from the outside primarily into the cement layer. Whilst some of the energy would also likely couple into other parts of the structure, the DAS should be able to resolve the acoustic energy travelling through the cement layer, and hence be able to check the structural integrity thereof.

Similar arrangements could also be made to check the integrity of other layers using external acoustic illumination.

In the above embodiments we have focussed on fluid flow carrying structures. In other embodiments, any other structure may be monitored, for example for structural integrity, using the acoustic illumination and DAS sensing techniques described. The invention is therefore not limited to the monitoring of fluid flow carrying structures, and extends to a method and system for monitoring a structure, comprising determining the generation of an acoustic wave; and at the same time as the generated acoustic wave is incident on the structure, sensing, using a distributed acoustic sensor, acoustic energy coupled into the structure from the incident generated acoustic wave.

Various modifications may be made to the above described embodiments to provide further embodiments, any and all of which are intended to be encompassed by the appended claims.

The invention claimed is:

1. A method of monitoring a fluid-flow carrying structure, the method comprising:
obtaining acoustic data corresponding to acoustic energy sensed using an optical fiber distributed acoustic sensor at the same time as an acoustic wave is incident on the structure, the acoustic energy being coupled into the fluid-flow carrying structure from the incident acoustic wave; and
calculating a speed of sound in a fluid flow within the structure from the acoustic data, the calculating comprising:
plotting the acoustic data as a two-dimensional space-time image;
applying a two dimensional Fourier transform to the two-dimensional space-time image to obtain a transformed image;
in the transformed image, identifying gradients in the transformed image, the identified gradients corresponding to the respective speeds of sound, or at least a property or derivative thereof, of the coupled acoustic energy in the fluid flow within the structure in opposite directions along the fluid flow carrying structure; and
calculating the fluid flow in dependence on a difference between the respective speeds of sound in the fluid flow in the opposite directions.

2. A system for monitoring a fluid-flow carrying structure, the system comprising:
a processor arranged in use to:
obtain acoustic data corresponding to acoustic energy sensed using an optical fiber distributed acoustic sensor at the same time as an acoustic wave is incident on the structure, the acoustic energy being coupled into the fluid-flow carrying structure from the incident acoustic wave; and
calculate a speed of sound in a fluid flow within the structure from the acoustic data, the calculating comprising:
plotting the acoustic data as a two-dimensional space-time image;
applying a two dimensional Fourier transform to the two-dimensional space-time image to obtain a transformed image;
in the transformed image, identifying gradients in the transformed image, the identified gradients corresponding to the respective speeds of sound, or at least a property or derivative thereof, of the coupled acoustic energy in the fluid flow within the structure in opposite directions along the fluid flow carrying structure; and
calculating the fluid flow in dependence on a difference between the respective speeds of sound in the fluid flow in the opposite directions.

* * * * *